United States Patent [19]

Lewis

[11] 4,411,153
[45] Oct. 25, 1983

[54] SCLEROMETER

[76] Inventor: Alfred H. Lewis, 1455 Sherbrooke W., Montreal, Quebec, Canada

[21] Appl. No.: 372,144

[22] Filed: Apr. 27, 1982

[51] Int. Cl.³ .............................................. G01N 3/48
[52] U.S. Cl. ........................................................ 73/79
[58] Field of Search .......................... 73/78, 79, 82, 12

[56] References Cited

U.S. PATENT DOCUMENTS 3,879,982  4/1975  Schmidt ................................. 73/79
4,034,603  7/1977  Leeb et al. ............................. 73/12

FOREIGN PATENT DOCUMENTS 1187394  2/1965  Fed. Rep. of Germany .......... 73/79

Primary Examiner—S. Clement Swisher
Attorney, Agent, or Firm—Robert J. Schaap; Eric Fincham

[57] ABSTRACT

A hardness testing device which includes a guiding member having an elongated passage with a hammer or striker freely movable therein is a taught. The hammer is held in a desired position and is released to strike the material whose hardness is to be tested. The rebound height indicates the hardness of the material and this rebound height is measured by correlating the time between sound waves emitted by the striker on its first impact and second impact on the material to be tested.

7 Claims, 4 Drawing Figures

SCLEROMETER

The present invention relates to a method and apparatus for texting the hardness of materials.

Many different hardness testing methods and apparatuses are known in the art, including both static and dynamic methods. As is taught in U.S. Pat. No. 1,154,663 to SHORE, a scleroscope utilizes a hammer or striker, means for raising and retaining the hammer at a given height above the material to be tested, and means for releasing the striker which then falls by gravity onto the material whose hardness is to be tested. The height of the rebound of the striker from the material indicates the hardness of the same. Basically, all scleroscope dynamic methods and apparatuses utilize either this rebound height as a measure of the material hardness or alternatively, utilize the differences between the striker velocity on impact and rebound.

As will be appreciated, considerable difficulties can be encountered in accurately determining the rebound height by visual means. Accordingly, there have been many proposals in the art for means to convert the rebound height into a suitable read-out which may be taken by an unskilled operator. The various proposals advanced in the art include mechanical means such as taught in the aforementioned U.S. Patent as well as other means such as photo-electric, electrical etc.

It is an object of the present invention to provide a scleroscope device which will accurately measure the rebound height of a hammer or striker from the material to be tested and which device employs a time measurement of sound waves between the two impacts upon the tested materials.

It is a further object of the present invention to provide a scleroscope which is compact and provides a visual read-out of the hardness of the material to be tested.

According to the present invention, there is provided a hardness tester which, in common with known hardness testers, includes a guiding member having an elongated passage therein with a hammer or striker freely moveable in the elongated passage. The hammer is held in a desired position by suitable retaining means such that the hammer is remote from one end of the passage. Means are provided for releasing the hammer or striker from its retained position to permit the hammer or striker to freely move under gravity to the end and to thereby strike the object the hardness of which is to be tested. The device further includes a timer having associated therewith first means for activating the timer when a first sound wave impinges thereon and second means associated with the timer for stopping the timer when a second or further sound wave impinges thereon. Preferably, the device includes means for converting the time between the first and second means into a visual read-out.

In greater detail, the guiding member may be a conventional housing of a suitable size and configuration having an internal elongated passageway therein. The passageway is sized to receive the hammer or striker; the details of such a structure is known to those skilled in the art and will not be elaborated on herein. It suffices to say that the hammer or striker should be freely moveable under the force of gravity within the passageway and should have minimal frictional engagement with the walls defining the passageway.

As is conventional, the hammer or striker will be formed of a hard metallic material. Several different means may be utilized for retaining the hammer or striker in its remote position preparatory to release the same to strike the material to be tested. The devices known for retaining the hammer in its desired position may include known mechanical assemblies or, in a preferred embodiment of the present invention, a permanent magnet may be utilized.

The scleroscope will also include means for releasing the hammer from its retained position and again, known means may be employed. In conjunction with the preferred magnet embodiment for the retaining means, the release means may, in one embodiment, include a solenoid to raise the permanent magnet against the spring pressure upon activation of the solenoid. Alternatively, mechanical means may be employed to raise the magnet. The hammer or striker would be arranged so as not to be capable of rising or moving further and accordingly, once the magnetic contact with the permanent magnet is broken the hammer or striker would be free to fall through the passageway to strike the material to be tested. A spring member or like means may be used to move the magnet.

The device further includes a timer for measuring the elapsed time between the first impact of the hammer or striker on the surface to be tested and the second impact thereon after rebound. In particular, the device of the present invention utilizes a measurement of the time between sound waves produced by the two impacts of the hammer or striker on the material to be tested. To this end, the device will include sound sensitive means such as microphone which is activated by the sound waves of the first impact which in turn will be operatively associated with a transducer to commence activation of a timer. The second sound waves following the second impact of the hammer will function to stop the timer. The elasped time between the two impacts is directly proportional to the square root of the rebound height and is therefore a measure of this height. This naturally can be correlated to the hardness of the material to be tested. In order to return the striker or hammer to its original position, the device can be inverted causing the hammer or striker to return to its retained position.

The device will also preferably include means for converting the elapsed time measurement to some form of read-out. As will be appreciated by those knowledgeable in the art, conventional electronic circuitry can be utilized to give the desired read-out.

Having thus generally described the invention, reference will be made to the accompanying drawings illustrating an embodiment thereof, in which.

Figure 2:
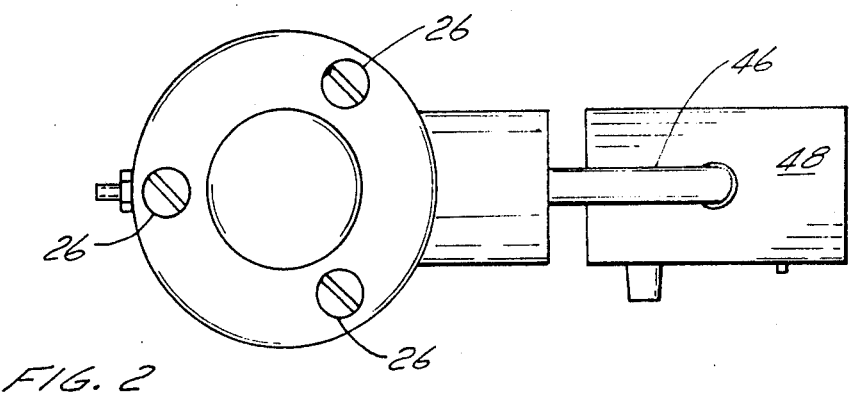
FIG. 2 is a top view thereof.
Figure 1:
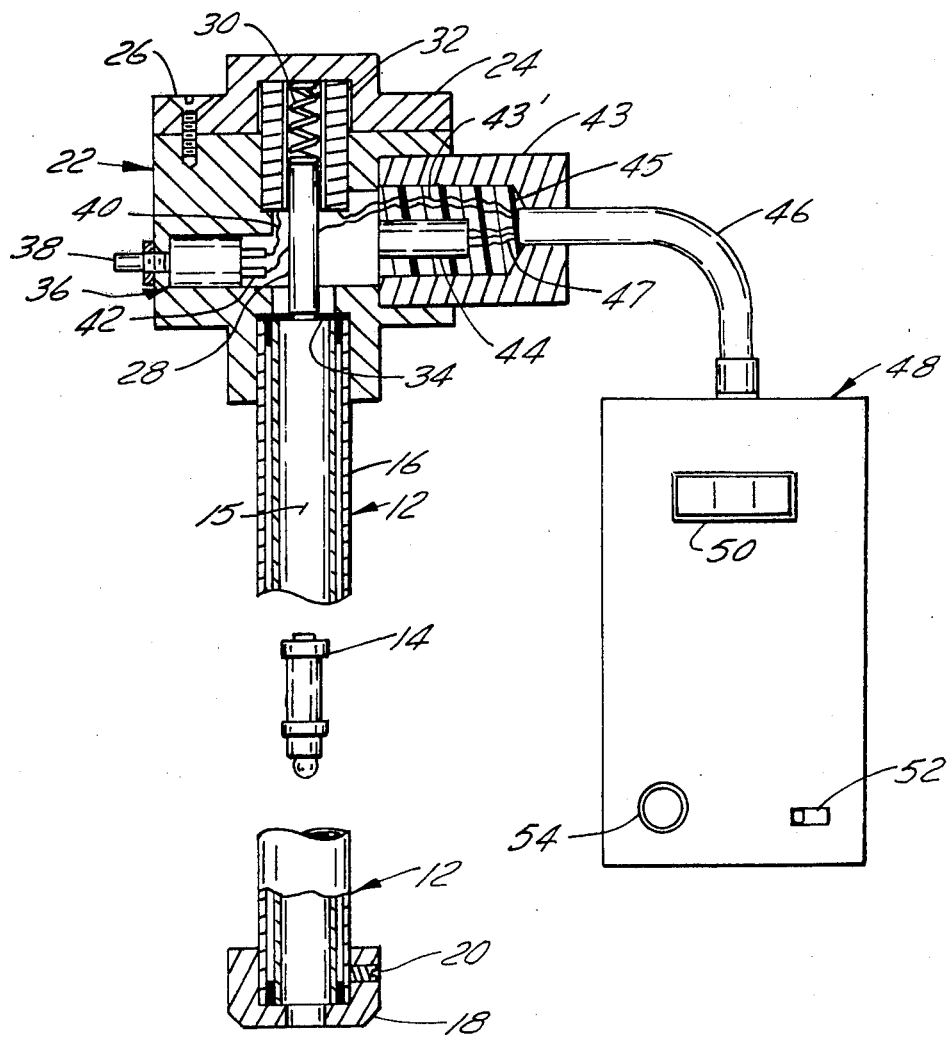
FIG. 1 is a cross-sectional view of a scleroscope according to the present invention.

Referring initially to FIG. 1 and by reference numerals thereto, the scleroscope includes a guiding member generally designated by reference numeral 12; guiding member 12 has an interior wall 16 defining a cavity or passageway 15 in which there is placed a hammer or striker 14. Hammer 14 is freely movable within passageway 15 under the force of gravity.

Situated at the "lower" end of guiding member 12 is lower end cap 18 which functions to prevent hammer 14 from exiting therethrough. A screw 20 is adapted to retain lower end cap 18 on the end of guiding member 12.

Situated at the opposed end of guiding member 12 is an upper housing generally designated by reference numeral 22. An upper cap 24 is secured to housing 22 by means of screws 26. Upper housing 22 and cap 24 have mounted therein a coil spring 30 and a solenoid 32, interiorly of which is a permanent magnet 28. As may be seen from FIG. 1, solenoid 32 is mounted within housing 22 and upper end cap 24 while mounted interiorly thereof is a coil spring 30, one end of which abuts upper end cap 24 while the other end thereof abuts permanent magnet 28. The opposite end of permanent magnet 28 abuts a washer 34 which is retained in its desired position covering the upper end of guiding member 12 by means of upper housing 22. Washer 34 is preferably of a suitable non-magnetic material such as rubber and has a centrally located aperture sized to prevent the passage of both permanent magnet 28 and hammer 14 therethrough.

Mounted within upper housing 22 is a switch member 36 having a push button 38 associated therewith, a first lead 40 operatively connects switch 36 and solenoid 32, and a second lead 42 operatively connects to timer 48 as will be discussed in greater detail hereinbelow. A third lead 43 connects solenoid 32 and timer 48.

Also mounted within upper housing 22 is a sub housing generally designated by reference numeral 43. Sub housing 43 has mounted therein microphone 44, which microphone 44 is surrounded by a suitable sound insulation 45. A plurality of leads 47 operatively interconnect microphone 44 and timer 48. As may be seen in FIG. 1, leads 42, 45 and 47 pass through a conduit 46 having one end mounted in sub housing 43 to timer 48.

Timer 48 has associated therewith a visual read-out generally designated by reference numeral 50. Read-out 50 may be suitable LED. Furthermore, timer 48 may include an on-off switch 52 and a reset button 54.

Figure 3:
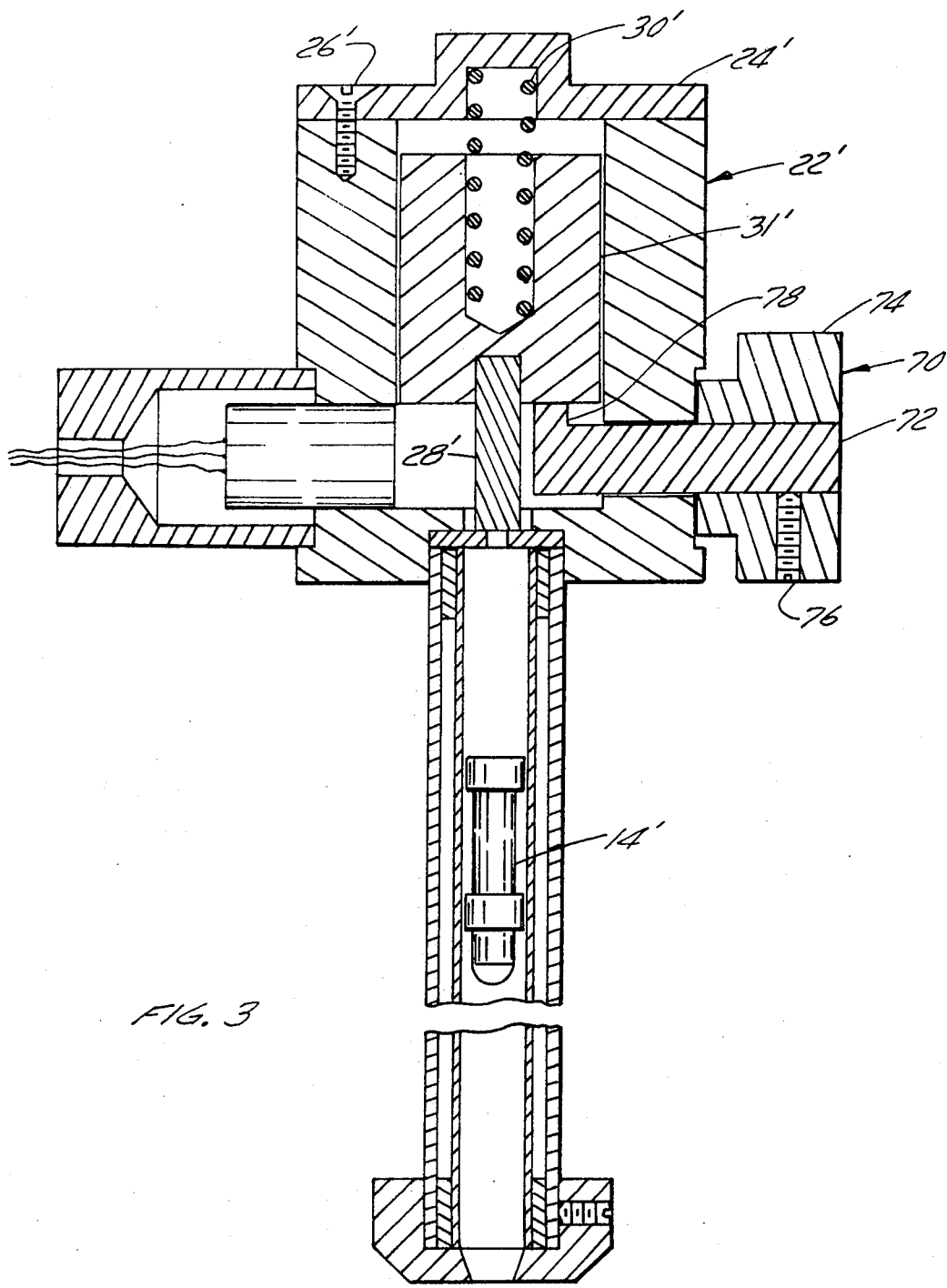
FIG. 3 is a cross-sectional view of a further embodiment.

Referring to the embodiment illustrated in FIG. 3, there is provided an upper housing 22', having upper cap 24' secured thereto by means of screws 26'. A permanent magnet 28' is press-fitted into a plunger 31' which is movable within upper housing 22'. Spring 30' fits within an aperture provided in end cap 24' and plunger 31' as may be seen in FIG. 3.

The embodiment of FIG. 3 also includes a cam device generally designated by reference numeral 70. Cam device 70 includes a nob 74 attached by means of screw 76 to cam shaft 72 which has at one end thereof a cam 78. Cam 78 functions to raise plunger 31' against the pressure of spring 30' whereby permanent magnet 28' is also raised to thereby release striker 14'. A further rotation of cam 78 which naturally permit plunger 31' and permanent magnet 28' to return to the lower position due to the action of spring 30' and thereby retain striker 14' in its "set" position.

Figure 4:
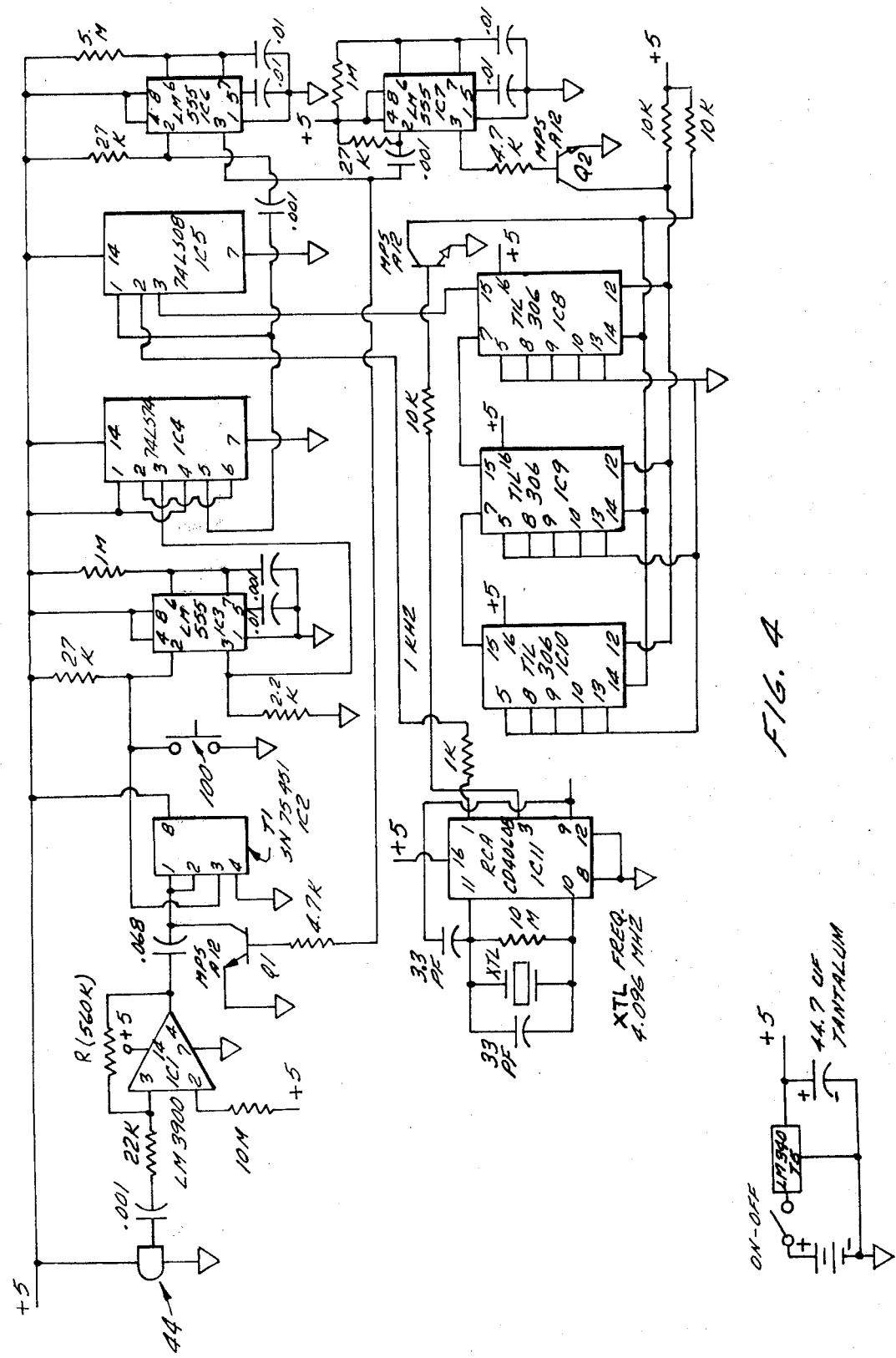
FIG. 4 is a schematic view of an electric circuit suitable for use with the scleroscope of the invention.

FIG. 4 illustrates a typical electronic circuit which may be utilized with the device of the present invention. In the figure IC 11 is a binary counter and oscillator which divides the crystal frequency of 4.096 Mhz to 1,000 pulses per second. The timing between the first two bounces of the striker on the piece under test is measured in milliseconds by pulse-counting timers (IC 8, IC 9 and IC 10) through AND gate IC 5. The sound waves from the bounces are picked up by the microphone 44 and amplified by IC 1. The AC signal changes shape to a square wave form by peripheral driver IC 2.

The initial pulse from the first bounce triggers timer IC 3 which causes the DK flip-flop IC 4 to go HIGH and this in turn closes the AND gate IC 5 which activates the counting of the displays. The second bounce causes the flip-flop to go LOW and this triggers IC 6 which sends the signal to transistor Q 1 causes the microphone output to go to ground, thus stopping all further sound pulses from reach IC 2. The LOW state of IC 4 opens the gate IC 5 thus stopping the counters so that the displays now register the elapsed time in milliseconds between bounces. Timer IC 6 locks the output for 5 or 6 seconds after which it deactivates Q 1 and triggers timer IC 7 which sends a pulse to transister Q 2, thus blanking the displays to 0 by momentary grounding of pin 12. The circuit is now ready for the next test. Pin 3 of IC 11 supplies pulses 250 cycles per second to flash the displays in order to minimize the current drain on the power source which typically is a battery.

A momentary start-stop switch 100 is utilized to stop the counters in the event of inadvertent triggering by stray sounds. Momentary closing of switch 100 grounds the output of IC 2. If IC 4 is at HIGH and the display is counting, closure of the switch causes IC 4 to go LOW which stops the count and drives the display to 0 after the five or six seconds delay. If IC 4 is at LOW the display shows a stationary reading and one closure of the switch is required to make IC 4 go HIGH which will start the display counting, followed by a second closure of the switch 100 to make IC 4 go LOW which again stops the count and sets the display to 0.

It will be understood that the above-described embodiments were for purposes of illustration only and that changes and modifications may be made thereto without departing from the spirit and scope of the invention.

I claim:

1. A hardness tester comprising a guiding member having an elongated passageway therein, a striker freely movable in said elongated passageway, means for retaining said striker in a position remote from one end of said passageway, means for releasing said striker from said retaining means to permit said striker to freely move to said one end, timer means, said timer means having first means associated therewith to activate the timer when a first sound wave impinges thereon, second means to stop said timer when a further sound wave impinges thereon.

2. The tester of claim 1 further including means to automatically reset said timer to zero after a fixed time delay period.

3. The tester of claim 1 further including a means to reset said timer to zero if said timer is inadvertently triggered.

4. The tester of claim 1, 2 or 3, wherein said retaining means comprises a permanent magnet.

5. The tester of claim 1, 2 or 3, wherein said means for releasing said striker comprises a cam member operative to move said retaining means.

6. The tester of claim 1, 2 or 3, further including means associated with said timer means to convert elapsed time to a digital read-out.

7. The device of claim 1, 2 or 3, further including spring means for moving said retaining means back to a desired position.

* * * * *